(12) United States Patent
Guit et al.

(10) Patent No.: US 6,191,274 B1
(45) Date of Patent: Feb. 20, 2001

(54) RECOVERY OF ε-CAPROLACTAM

(75) Inventors: Rudolf P. M. Guit, Maastricht; Yvonne H. Frentzen, Venlo, both of (NL)

(73) Assignees: DSM N.V., Heerlen (NL); E.I. du Pont Nemous and Company, Wilmington, DE (US)

( * ) Notice: Under 35 U.S.C. 154(b), the term of this patent shall be extended for 0 days.

(21) Appl. No.: 09/134,756

(22) Filed: Aug. 17, 1998

Related U.S. Application Data

(63) Continuation of application No. PCT/NL97/00033, filed on Feb. 5, 1997.

(30) Foreign Application Priority Data

| Feb. 17, 1996 | (MY) | PI 960 0650 |
| Sep. 2, 1996 | (EP) | 96202436 |
| Oct. 21, 1996 | (EP) | 96202931 |

(51) Int. Cl.⁷ .................................................. C07D 201/16
(52) U.S. Cl. ............................................................ 540/540
(58) Field of Search ............................................ 540/540

(56) References Cited

U.S. PATENT DOCUMENTS

| 3,485,821 | 12/1969 | Sheehan | 260/239.3 |
| 3,761,467 | 9/1973 | Williams et al. | 260/239.3 |
| 3,912,721 | 10/1975 | Mattone et al. | 260/239.3 |
| 4,013,640 | 3/1977 | Somekh | 260/239.3 |
| 4,036,830 | 7/1977 | de Rooij et al. | 260/239.3 |
| 4,072,678 | 2/1978 | Oyama et al. | 260/239.3 |
| 4,153,600 | 5/1979 | Geurts et al. | 260/239.3 |
| 4,366,306 | * 12/1982 | Smith | 528/315 |
| 4,730,040 | 3/1988 | Vagt et al. | 540/538 |
| 5,359,062 | 10/1994 | Fuchs et al. | 540/540 |

FOREIGN PATENT DOCUMENTS

| 1 770 088 | 9/1971 | (DE) . |
| 1 620 300 | 3/1972 | (DE) . |
| 2 332 973 | 1/1974 | (DE) . |
| 26 19 234 | 11/1976 | (DE) . |
| 26 28 085 | 1/1977 | (DE) . |
| 28 01 256 | 7/1978 | (DE) . |
| 0 242 505 | 10/1987 | (EP) . |
| 0 568 882 | 11/1993 | (EP) . |
| 1121109 | 7/1968 | (GB) . |
| 1198428 | 7/1970 | (GB) . |
| 1 251 258 | 10/1971 | (GB) . |

* cited by examiner

*Primary Examiner*—Mukund J. Shah
*Assistant Examiner*—Bruck Kifle
(74) *Attorney, Agent, or Firm*—Pillsbury Winthrop LLP

(57) ABSTRACT

Process to separate ε-caprolactam from an aqueous mixture containing ε-caprolactam and at least 0.5 wt % oligomers, wherein the separation is performed by extraction using an organic extraction agent. The aqueous mixture may be obtained in a process to prepare ε-caprolactam starting from 6-aminocapronitrile or in a process to prepare ε-caprolactam starting from 6-aminocaproic acid.

6 Claims, No Drawings

RECOVERY OF ε-CAPROLACTAM

This is a Continuation of: International Appln. No. PCT/NL97/00033 filed Feb. 5, 1997 which designated the U.S.

The invention relates to a process to separate ε-caprolactam from an aqueous mixture containing ε-caprolactam and at least 0.5 wt % oligomers.

Such a process is known from U.S. Pat. No. 5,495,016. In this patent publication a process is described in which 6-aminocapronitrile is converted into crude ε-caprolactam by reaction with water. The resulting aqueous mixture comprises ammonia, ε-caprolactam and oligomers. By first separating ammonia by distillation an aqueous mixture is obtained comprising ε-caprolactam and said oligomers. Subsequently ε-caprolactam is separated from this mixture by distillation, in which the ε-caprolactam and water is recovered as the top product and oligomers are recovered in a concentrated mixture as bottom product.

A disadvantage of this process is that at the high reboiler temperatures of the distillation column ε-caprolactam will easily convert to more oligomers (2 wt. % absolute according to Example I of U.S. Pat. No. 5,495,016). Furthermore fouling of pipes and other process equipment because of solidification of the oligomers cannot be easily avoided.

The object of the invention is a process for the separation of ε-caprolactam from aqueous mixtures comprising also oligomers in which the above mentioned disadvantages are avoided.

This object is achieved in that the separation is performed by extraction using an organic extraction agent.

It has been found that extraction is an efficient method of separating ε-caprolactam from oligomers in aqueous mixtures. Furthermore the oligomers are obtained in an aqueous mixture which can be easily further processed to yield more ε-caprolactam.

Extraction is a known method of separating ε-caprolactam from the reaction mixture obtained by the Beckmann rearrangement of cyclohexane oxime with sulfuric acid or oleum. After neutralization of the discharged rearrangement reaction mixture with ammonia, the ε-caprolactam is separated from the ammonium sulfate by extraction with an organic solvent, such as benzene. No oligomers are formed in this process.

In addition to the Beckmann rearrangement of cyclohexanone oxime to ε-caprolactam, there are further synthesis routes leading to ε-caprolactam. Possible routes which yield an aqueous mixture are the cyclization of 6-aminocaproic acid as described in U.S. Pat. No. 4,730,040 and the reaction of 6-aminocapronitrile as described in the earlier mentioned U.S. Pat. No. 5,496,941. Because the by-product spectrum of the here described processes differ completely from that of ε-caprolactam prepared by a Beckmann rearrangement, it was not to be expected that extraction in general would be a favorable method of separating ε-caprolactam from 6-aminocaproic acid and from oligomers. U.S. Pat. No. 5,495,016 only mentiones distillation as separation method.

U.S. Pat. No. 4,730,040 mentions the extraction of ε-caprolactam from aqueous mixtures containing ε-caprolactam using chloroform. This patent is however silent if ε-caprolactam can also be separated from aqueous mixtures also containing oligomers.

U.S. Pat. No. 3,485,821 describes a process for the preparation of ε-caprolactam by heating an aqueous mixture of 6-aminocaproic acid. In the examples ε-caprolactam is isolated by extraction with chloroform. Only in Example 13 of this patent publication some polyamide is also present in the aqueous ε-caprolactam containing mixture. No extraction is performed in this example to isolate ε-caprolactam. The polyamide was separated from the aqueous mixture by cooling and filtration.

U.S. Pat. No. 4,013,640 describes the extraction of water soluble amides, such as ε-caprolactam, n-butyramide and n-valeramide, from an aqueous mixture using alkyl phenol solvents as the extraction agent. This patent publication mentions a wide range of linear and cyclic amides which can be extracted. It was therefore not to be expected that ε-caprolactam could be succesfully separated from other amides such as oligomers.

The oligomers are generally oligomers (dimers and trimers mostly) of 6-aminocaproic acid or of 6-aminocaproamide.

The concentration oligomers in the aqueous mixture is higher than 0.5 wt. %. Preferably not more than 10 wt. % and most preferably not more than 5 wt. % of oligomers are present in the aqueous mixture.

The invention relates especially to the separation of ε-caprolactam from aqueous mixtures obtained in (a) a process to prepare ε-caprolactam in which 6-aminocapronitrile is converted into crude ε-caprolactam by reaction with water as described in for example U.S. Pat. No. 5,495,016, (b) a process to prepare ε-caprolactam by cyclization of 6-aminocaproic acid in water as described in for example U.S. Pat. No. 4,730,040 or (c) in a comparable process as under (b) in which the starting mixture comprises 6-aminocaproic acid and 6-aminocaproamide.

The aqueous mixture obtained in processes (a) and (c) will also contain ammonia which is a side-product of the reaction to ε-caprolactam starting from 6-aminocapronitrile or 6-aminocaproamide. It is advantageous to separate the ammonia prior to the extraction, for example by distillation or steam stripping. In the distillation any unconverted 6-aminocapronitrile (in process (a)) and part of the water will generally be separated as well. The concentration of the ε-caprolactam, optionally 6-aminocaproic acid, optionally 6-aminocaproamide and oligomers in the aqueous mixture obtained after such an ammonia separation will be preferably higher than 10 wt %.

In the event that the aqueous mixture is obtained starting from 6-aminocaproic acid or mixtures of 6-aminocaproic acid and 6-aminocaproamide, the conditions of such process are preferably as described below.

Preferably the concentration of ammonia and ammonia equivalents is below 5 wt. %. With ammonia equivalents is meant that every mol of a compound having a —C(O)—$NH_2$ group is calculated as a mol $NH_3$. The total molar amount of $NH_3$ thus calculated can be expressed in a weight % of $NH_3$. This number should be below 5 wt. % and preferably below 3 wt. %.

The concentration of ε-caprolactam, 6-aminocaproic acid, 6-aminocaproamide and oligomers is preferably between 5–50 wt. % and more preferably between 10–35 wt. %. The concentration of ε-caprolactam is preferably between 5–30 wt. %.

The temperature is preferably between 270 and 350° C., more preferably higher than 290° C.

The pressure is preferably between 5.0 and 20 MPa. Normally the pressure will be greater than or equal to the resulting pressure of the liquid reaction mixture and the temperature employed.

The reaction to ε-caprolactam can be performed continuously. The aqueous mixture obtained in the extraction according to the invention is preferably recycled to the cyclization processes as (a)–(c) here described. It has been found that the compounds, for example 6-aminocaproic acid, 6-aminocaproamide and oligomers which are present in this mixture can react to ε-caprolactam in a high yield. Thus by using extraction to isolate ε-caprolactam a valuable recycle stream is also obtained which can be succesfully used to prepare more ε-caprolactam.

The aqueous phase obtained in the extraction will contain oligomers and optionally 6-aminocaproamide and/or 6-aminocaproic acid.

The extraction agent is preferably an organic solvent which is substantially immiscible with water. By substantially immiscible is here meant that the mixture of organic solvent and the aqueous mixture results in two segregated phases at the extraction temperature. Preferable the mutual solubility under the conditions of the extraction is not higher than 30 wt. % and more preferably less than 20 wt. %.

Possible extraction agents are aromatic solvents, for example benzene, toluene, xylene; ethers, for example diethylether, methyl tert-buthylether; Preferably chlorinated hydrocarbons with 1 to 10 carbon atoms are used. Examples are chloroform, dichloromethane and 1,1,1-trichloroethane.

Another class of preferred extraction agents are phenol and even more preferred are alkyl phenols. A preferred class of alkyl phenols have a boiling point which is higher than that of ε-caprolactam. It has been found that ε-caprolactam can be separated from especially oligomers, using this class of extraction agents.

The extraction agent can preferably be an alkyl phenol having a boiling point higher than the boiling point of ε-caprolactam, which is 270° C. at 1 bar. Alkyl phenols have a high boiling point at atmospheric pressure. Therefore, boiling points are advantageously compared at reduced pressures of, for example, 1.3 kPa (10 mmHg). Caprolactam has a boiling point of 140° C. at 10 mmHg, while dodecyl phenol, for example, has a boiling point of 190° C. at that pressure. By preference, the boiling point of the alkyl phenol is more than about 5° C., and in particular, more than about 15° C. higher than the caprolactam boiling point at 1.3 kPa (10 mmHg). The upper limit to the normal boiling point of the alkyl phenol is about 400° C. The alkyl phenol preferably is non-azeotropic with ε-caprolactam. Mixtures of alkyl phenols can also be used.

An alkyl phenol is phenol substituted with one or more alkyl groups. The total number of carbon atoms of the alkyl group(s) is preferably between 6–25 and more preferably between 9–15. Examples of specific alkyl phenolic compounds include dodecyl phenol, octyl phenol, nonyl phenol, n-hexyl phenol, 2,4-diisobutyl phenol, 2-methyl-4,6-di-tert-butyl phenol, 3-ethyl-4,6-di-tert-butyl phenol, 2,4,6-tri-tert-butyl phenol, and mixtures of any thereof. U.S. Pat. No. 4,013,640 discloses additional alkyl phenols, the complete disclosure of which is hereby incorporated by reference.

More preferred extracion agents are (cyclic) aliphatic organic compounds having one or more hydroxy groups which are liquid under the extraction conditions and substantially immiscible with water. Such (poly)alcohols have preferably 5–12 carbon atoms. These extraction agents are preferred because they have a better extraction efficiency than the chloronated organic compounds and are more inert than most of the phenol like compounds as described above. These extraction agents are furthermore preferred because their use does not result in any environmetnal objections. Preferably one or two and more preferably only one hydroxy group is present. Examples of compounds having two hydroxy groups are hexanediol, nonanediol, neopentylglycol, methyl-methylpropanediol, ethyl-methylpropanediol or butyl-methylpropanediol. Examples of compounds having one hydroxy group are cyclohexanol, 4-methyl-2-pentanol, 2-ethyl-1-hexanol, 2-propyl-1-heptanol, n-octanol, iso-nonylalcohol, n-decylalcohol and mixtures of linear and branched $C_8$-alcohols, mixtures of linear and branched $C_9$-alcohols and mixtures of linear and branched $C_{10}$-alcohols. Mixtures of the above mentioned alcohols can also be used.

When the aqueous mixture contains high amounts of 6-aminocaproamide and/or oligomers thereof it is preferred to perform a back wash on the ε-caprolactam containing (poly)alcohol phase after the extraction. This is because part of the 6-aminocaproamide and its oligomers tend to be extracted by the alcohol phase. A back wash can be performed by extracting the alcohol phase containing the ε-caprolactam with water. This can be performed in a continuously operated process by adding water to the top of an extraction column while the aqueous mixture is fed at a lower point of the column. The back wash can also be performed in a seperate column.

The amount of organic extraction agent is not particularly limited provided that the advantages of the present invention can be achieved. The upper limit, for example, is not believed critical but depends on process economy.

The extraction step is carried out at a temperature which is higher than the melting point of the organic extraction agent. The temperature of extraction can be generally between room temperature and 200° C. and preferably between 20 and 170° C.

The pressure during the extraction step is not generally critical and can be, for example, between about 0.1 MPa and about 2.0 MPa, and preferably, between about 0.1 MPa and about 0.5 MPa.

The extraction can be carried out in well known extraction apparatus, for example a counter current column, a series of mixer settlers, rotating disc contactors or pulsed packed columns.

The extraction step yields a ε-caprolactam-containing organic phase which, in general, contains up to 50 wt. % ε-caprolactam.

After the extraction ε-caprolactam may be recovered from the organic extraction agent by known separation methods, for example distillation and extraction. Preferably distillation is used. Especially when a higher boiling extraction agent is used as described above.

The organic phase is preferably reused in the extraction according to the invention. In order to avoid a build-up of high boiling products in the recirculating organic extraction agent a purge or a separate purification may be performed.

The liquid ε-caprolactam obtained in the distillation may be subsequently further purified as for example exemplified in U.S. Pat. No. 5,496,941.

In one preferred embodiment, the purification of the extracted and distilled ε-caprolactam comprises the following steps:

1) contacting ε-caprolactam at from 30 to 80° C. and from 0.1 to 0.5 MPa over an ion exchanger containing terminal acid groups,
2) treating the mixture obtained in step (1) with hydrogen at from 50° to 150° C. and from 0.15–25 MPa in the presence of a hydrogenation catalyst and
3) separating water and other light components by distillation
4) isolating ε-caprolactam by distillation.

The order of the ion exchange step (1) and hydrogenation step (2) can be reversed if desired. Steps (1) and (2) can be optionally performed in water or another solvent, for example the extraction agent as described above. This purification procedure results in ε-caprolactam of very good quality. The ion exchange and hydrogenation treatment are known methods for purifying ε-caprolactam obtained by Beckmann rearrangement and can be performed by these well known methods.

In a second preferred embodiment, the purification of the distilled ε-caprolactam is achieved by crystallization in a process of concentrating. The crystallized ε-caprolactam resulting from concentrating is generally sufficiently pure to be used directly. After crystallization, it may be necessary to purify the mother liquor by, for example, recycling it to the aqueous solution before the extraction with the alkyl phenol. The mother liquor can be purified, for example by means of distillation.

The inventions will now be elucidated by means of the following non-restrictive examples.

The composition of the resulting mixtures of the experiments are sometimes expressed in mol percentages. The molar percentage of a component is represented by the molar fraction (* 100%) which can theoretically convert to ε-caprolactam. For example, 50 mol 6-aminocaproic acid and 25 mol dimers can contribute to 100 mol. ε-caprolactam. The molar contribution will be 50 mol % 6-aminocaproic acid and 50 mol % dimers (totaling 100 mol %).

EXAMPLE I 200 ml of a mixture of 20 wt. % ε-caprolactam, 0.6 wt. % oligomers and 5 wt. % 6-aminocaproic acid in water was mixed well, long enough to reach equilibrium, with 200 ml chloroform at room temperature and 0.1 MPa. The water phase was separated from the chloroform by phase separation. The water phase was again mixed with 200 ml chloroform as above and separated from the chloroform by phase separation. The two chloroform phases were combined and analyzed by high pressure liquid chromatography (HPLC). The water phase was also analyzed and the partition coefficient of ε-caprolactam was 0.74. The partition coefficient is defined as the concentration in the organic extraction agent divided by the concentration in the aqueous phase at (almost) equilibirum conditions. No detectable amount of 6-aminocaproic acid or oligomers (<0.01 wt. %) was found in the chloroform phase.

EXAMPLE II

Example I was repeated with dichloromethane. The partition coefficient was 0.84. No detectable amount of 6-aminocaproic acid or oligomers (<0.01 wt. %) was found in the dichloromethane phase.

EXAMPLE III

Example I was repeated with methyl tert-butylether. The partition coefficient was 0.1. No detectable amount of 6-aminocaproic acid or oligomers (<0.01 wt. %) was found in the tert-butylether phase.

EXAMPLE IV

An aqueous mixture containing 15 wt. % 6-aminocaproic acid and 1 wt. % ammonia was continuosly fed at a rate of 630 g/hr to a plugflow reactor (almost no backmixing) at a constant temperature of 300° C. (maintained with the use of an oil bath), a pressure of 10 MPa and at a residence time of 30 minutes. The molar yield to ε-caprolactam was 81 mol %. 12 mol % oligomers and 7 mol % of 6-aminocaproic acid and 6-aminocaproamide was present. 200 ml of this mixture was subjected to an extraction as described in Example I. The partition coefficient for ε-caprolactam was as in Example I. No detectable amounts (<0.01 wt. %) of 6-aminocaproic acid, 6-aminocaproamide or oligomers were found in the chloroform phase.

EXPERIMENT V

Example I was repeated using the aqueous mixture obtained in Example 1 of U.S. Pat. No. 5,495,016 named "mixture 1" containing 90 wt. % water, 7,6 wt. % ε-caprolactam and 2,4 wt. % high boilers (oligomers). The partition coefficient for ε-caprolactam was as in Example I and no detectable amount of high boilers (oligomers) or 6-aminocaproic acid was found in the chloroform phase.

EXAMPLE VI

Example V was repeated at 80° C. using the same volume of dodecylphenol. The partition coefficient of ε-caprolactam was about 11. No detectable amount of oligomer was present in the organic phase.

Examples I–VI illustrate that ε-caprolactam can be succesfully separated from aqueous mixtures containing 6-aminocaproic acid, 6-aminocaproamide and oligomers. These batch examples also show that an almost 100% separation of ε-caprolactam is possible in a continuously operated extraction; for example in a counter current extraction column or in a series of mixer/settlers.

EXAMPLE VII

A mixture having a composition of 21.5 mol % 6-aminocaproic acid (6ACA), 45.9 mol % 6-aminocaproamide (6ACAM), 27.5 mol % ε-caprolactam (CAP), 2.1 mol % methyl 6-aminocaproate (M6AC) and 3.0 mol % oligomers with a total concentration of 12.4 wt. % of these compounds in water was continuously fed at a rate of 571 g/hr together with a recycle stream (see below) to the top of a steamstripper column (operated at 0.1 MPa). Steam was generated in a reboiler of the column and no additional water was added. The liquid bottom stream which left the steamstripper (rate 626 g/hr) did not contain any detectable amounts of methanol and ammonia. This aqueous stream consisted of 12.7 wt. % of 6ACA, 6ACAM, M6AC, CAP and oligomers.

This aqueous mixture was subsequently continuously fed to a cyclization reactor, a plugflow reactor (almost no backmixing), at a constant temperature of 320° C. (maintained with the use of an oil bath), a pressure of 12 MPa and at a residence time of 30 minutes. After separating ammonia and methanol from the effluent by distillation the liquid aqueous stream contained 15.1 wt. % products of which 89 mol % ε-caprolactam, 8 mol % oligomers and 3 mol % of 6ACA(M).

This aqueous mixture was subsequently fed (480 g/hr) to the bottom of a continuously operated counter current extraction column. To the top of this column (having 20 theoretical plates) chloroform was fed at a rate of 770 ml/hr. ε-caprolactam was extracted to the chloroform phase with a more than 99% yield. Pratically all of the 6-aminocaproic acid, 6-aminocaproamide and oligomers remained in the aqueous phase. This aqueous mixture obtained in the extraction was recycled at a rate of 416 g/hr to the steam stripper column (see above).

EXAMPLE VIII 100 g of an aqueous mixture containing 12.2 wt. % ε-caprolactam, 0.77 wt. % 6-aminocaproic acid, 0.01 wt. %, 6-aminocaproamide and 0.68 wt. % oligomers (of 6-aminocaproic acid and 6-aminocaproamide) was mixed well, long enough to reach equilibrium, with 100 g of 4-methyl-2-pentanol at 20° C. and 0.1 MPa. The water and alcohol phase were analyzed by HPLC.

The partition coefficient of $\epsilon$-caprolactam was about 1.65 (The water phase contained 4.28 wt. % $\epsilon$-caprolactam and the alkanol phase contained 7.06 wt. % $\epsilon$-caprolactam). No detectable amounts of 6ACA, 6ACAM or oligomers).

The alcohol phase contained 7 wt. % water.

EXAMPLE IX

Example VIII was repeated using the same volume of 2-ethyl-1-hexanol as the extraction agent. The partition coefficient of $\epsilon$-caprolactam was 1.16 (the water phase contained 5.23 wt. % $\epsilon$-caprolactam and the alkanol phase contained 6.09 wt. % of 6ACA, 6ACAM and oligomers were found in the alcohol phase. The alcohol phase contained 2.9 wt. % water.

EXAMPLE X

Example VIII was repeated using an aqueous mixture containing 15.5 wt. % $\epsilon$-caprolactam, 5.2 wt. % 6-aminocaproic acid, 17.4 wt. % 6-aminocaproamide and 5.6 wt. % oligomers at 80° C.

The partition coefficient of $\epsilon$-caprolactam was 3.3. No detectable amounts of 6-aminocaproic acid and oligomers of 6-aminocaproic acid were found in the alcohol phase. The partition coefficient of 6-aminocaproamide and oligomer of 6-aminocaproamide was 0.45.

What is claimed is:

1. A process for separating $\epsilon$-caprolactam from an aqueous mixture containing $\epsilon$-caprolactam comprising:

reacting at least one member selected from the group consisting of 6-aminocapronitrile, 6-aminocaproic acid and 6-aminocaproamide in water to obtain an aqueous mixture comprising $\epsilon$-caprolactam and at least 0.5 wt % oligomers of amides;

separating $\epsilon$-caprolactam from the aqueous mixture by extraction using an organic compound with one or more hydroxy groups as an extraction agent.

2. A process according to claim 1, wherein the extraction agent is an alkyl phenol having one or more alkyl groups.

3. A process according to claim 2, wherein the boiling point of the alkyl phenol is more than 15° C. higher than the boiling point of $\epsilon$-caprolactam at 1.3 kPa (10 mm Hg).

4. A process according to claim 1 wherein a (poly)alcohol having 5–12 carbon atoms is used as an extraction agent.

5. A process according to claim 4 wherein 4-methyl-2-pentanol or 2-ethyl-1-hexanol is used as an extraction agent.

6. A process according to any one of claims 2–5, wherein the aqueous mixture contains 6-aminocaproamide and/or its oligomers, and the resulting $\epsilon$-caprolactam containing extraction agent phase is extracted with water.

* * * * *